(12) United States Patent
Letant et al.

(10) Patent No.: US 8,059,924 B1
(45) Date of Patent: Nov. 15, 2011

(54) MULTIPLEXED PHOTONIC MEMBRANES AND RELATED DETECTION METHODS FOR CHEMICAL AND/OR BIOLOGICAL SENSING APPLICATIONS

(75) Inventors: Sonia E. Letant, Livermore, CA (US); Tiziana C. Bond, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 576 days.

(21) Appl. No.: 12/206,337

(22) Filed: Sep. 8, 2008

Related U.S. Application Data

(60) Provisional application No. 60/993,740, filed on Sep. 13, 2007.

(51) Int. Cl.
G02B 6/00 (2006.01)
G01N 21/01 (2006.01)
H04J 14/02 (2006.01)
A61B 5/00 (2006.01)

(52) U.S. Cl. ............ 385/12; 385/14; 385/122; 385/130; 385/131; 356/244; 398/79; 600/310; 600/364; 600/407

(58) Field of Classification Search .................. 385/122, 385/129, 130, 131, 132, 14, 141, 6, 12; 356/244, 356/39, 40, 41, 42; 600/310, 364, 407; 398/79
See application file for complete search history.

(56) References Cited

U.S. PATENT DOCUMENTS

| | | | |
|---|---|---|---|
| 6,468,823 B1 | 10/2002 | Scherer et al. | 438/31 |
| 6,643,439 B2 | 11/2003 | Notomi et al. | 385/125 |
| 6,738,551 B2 | 5/2004 | Noda et al. | 385/130 |
| 6,785,432 B2 | 8/2004 | Letant et al. | 385/12 |
| 7,026,640 B2 * | 4/2006 | Nathan et al. | 257/9 |
| 7,155,076 B2 | 12/2006 | Letant et al. | 385/12 |
| 7,206,488 B1 | 4/2007 | Altug et al. | 385/131 |
| 7,289,221 B2 * | 10/2007 | Wang et al. | 356/477 |
| 7,492,979 B2 * | 2/2009 | Wang et al. | 385/12 |
| 2003/0143580 A1 * | 7/2003 | Straus | 435/6 |
| 2004/0021193 A1 * | 2/2004 | Nathan et al. | 257/499 |
| 2004/0067163 A1 * | 4/2004 | Prasad et al. | 422/58 |
| 2006/0072642 A1 * | 4/2006 | Wang et al. | 372/50.1 |
| 2009/0244532 A1 * | 10/2009 | Letant et al. | 356/244 |

OTHER PUBLICATIONS

Levine, M.J. et al., "Zero mode waveguides for single molecule analysis at high concentration", Science, 299, 2003.
Victor S.-Y. Lin et al., "A Porous Silicon-Based Optical Interferometric Biosensor", Science, vol. 278, Oct. 31, 1997, pp. 840-843.
Selena Chan et al., "Identification of Gram Negative Bacteria Using Nanoscale Siliconix Microcavities" J. Am. Chem. Soc. 2001, 123, pp. 11797-11798.

(Continued)

Primary Examiner — Brian Healy
(74) Attorney, Agent, or Firm — Eddie E. Scott

(57) ABSTRACT

Photonic detection systems and methods are shown. A flow through photonic membrane is provided with pores which are distributed along multiple regions. The pores of one region have walls to which a first type of target specific anchor can be attached, while pores of another region have walls to which a second type of target specific anchor can be attached. An additional region of pores without anchors can be provided, so that optical detection occurs differentially. A stack of photonic membranes is also provided. The diameter of the pores of one photonic membrane is larger than the diameter of the pores of another photonic membrane, thus allowing also determination of the size of a target organism flown through the stack of membranes.

11 Claims, 9 Drawing Sheets

OTHER PUBLICATIONS

Sonia E. Letant et al., "Enzyme Immobilization on Porous Silicon Surfaces", Adv. Mater., 16, No. 8, Apr. 19, 2004, pp. 689-693.

Sonia Letant et al., "Functionalized silicon membranes for selective bio-organism capture", Nature Materials, vol. 2, Jun. 2003, pp. 391-395.

F. Morhard et al. "Immobilization of antibodies in micropatterns for cell detection by optical diffraction", Sensors and Actuators B 70, 2000, pp. 232-242.

Bradley Schmidt et al., "Nanocavity in a silicon waveguide for ultrasensitive nanoparticle detection", Applied Physics Letters, vol. 85, No. 21, Nov. 22, 2004, pp. 4854-4856.

Mindy R. Lee et al., "Nanoscale microcavity sensor for single particle detection", Optics Letters, vol. 32, No. 22, Nov. 15, 2007, pp. 3284-3286.

Bradley R. Hart et al., "New method for attachment of biomolecule to porous silicon", Chem. Commun., 2003, pp. 322-323.

Marko Loncar et al., "Photonic crystal laser sources for chemical detection", Applied Physics Letters, vol. 82, No. 26, Jun. 30, 2003, pp. 4648-4650.

Leo L. Chan et al., "Self-referenced assay method for photonic crystal biosensors: Application to small molecule analytes" Sensors and Actuators B 120, 2007, pp. 392-398.

E. Chow et al., "Ultracompact biochemical sensor built with two-dimensional photonic crystal microcavity" Optics Letters, vol. 29, No. 10, May 15, 2004, pp. 1093-1095.

Baker, S., et al., Detection of Bio-organism stimulants using random binding on a defect-free photonic crystal, Applied Physics Letters 2010 (in press).

Letant, S., et al., Integration of porous silicon chips in an electronic artificial nose, Sensors and Actuators B 2000, 69: 193-198.

Nilsson, J., et al., Localized functionalization of single nanopores, Advanced Materials 2006, 18: 427-431.

Katz, A., In situ determination of refractive index and size of *Bacillus* spores by light transmission, Optics Letters 2005, 30: 589-591.
Grow, A., et al., New biochip technology for label-free detection of pathogens and their toxins, Journal of Microbiological Methods 2003, 221-233.
Nguyen, B., et al., Membrane-Based Electrochemical Nanobiosensor for the Detection of Virus, Anal. Chem. 2009, 81: 7226-7234.
Dorfner, D., et al., Silicon photonic crystal nanostructures for refractive Index sensing, Applied Physics Letters 2008, 93: 181103-1-181103-3.
Larsson, E., et al., Sensing Characteristics of NIR Localized Surface Plasmon Resonances in Gold Nanorings for Application as Ultrasensitive Biosensors, Nano Letters 2007, 7: 1256-1263.
Vollmer, F., et al., Single virus detection from the reactive shift of a whispering-gallery mode, PNAS 2008, 105: 20701-20704.
Hagino, H., et al., Effects of fluctuation in air hole radii and positions on optical characteristics in photonic crystal heterostructure nanocavities, Physical Review B 2009, 79: 085112-1-085112-8.
Rea, I., et al., Fabrication and characterization of a porous silicon based microarray for label-free optical monitoring of biomolecular interactions, Journal of Applied Physics 2010, 107: 014513-1-014513-4.
Guicheteau, J., et al., *Bacillus* Spore Classification via Surface-Enhanced Raman Spectroscopy and Principal Component Analysis, Applied Spectroscopy 2008, 62: 267-272.
Lee, J., Real-time detection of airborne viruses on a mass-sensitive device, Applied Physics Letters 2008, 93: 013901-1-013901-3.
Fitch, J., et al., Technology Challenges in Responding to Biological or Chemical Attacks in the Civilian Sector, Science 2003, 302: 1350-1354.
Hodges, L., et al., National validation study of a swab protocol for the recovery of *Bacillus* anthracis spores from surfaces, Journal of Microbiological Methods 2010, 141-146.
Cyrklaff, M., et al., Cryo-electron tomography of vaccinia virus, PNAS 2005, 102: 2272-2777.
Schwartz, M., et al., The Smart Petri Dish: A Nanostructured Photonic Crystal for Real-Time Monitoring of Living Cells, Langmuir 2006, 22: 7084-7090.
Buttner, M., et al., Determination of the Efficacy of Two Building Decontamination Strategies by Surface Sampling with Culture and Quantitative PCR Analysis, Applied and Environmental Microbiology 2004, 70: 4740-4747.
Lee, M., et al., Nanoscale microcavity sensor for single particle detection, Optics Letters 2007, 32: 3284-3286.
Mortensen, N., et al., Liquid-infiltrated photonic crystals: enhanced light-matter interactions for lab-on-a-chip applications, Microfluid Nanofluid 2008, 4: 117-127.
Skottrup, P., et al., Towards on-site pathogen detection using antibody-based sensors, Biosensors and Bioelectronics 2008, 24: 339-348.
Golightly, R., et al., Surface-Enhanced Raman Spectroscopy and Homeland Security: A Perfect Match?, AC Nano 2009, 3: 2859-2869.
van der Heijden, R., et al., InP-based two-dimensional photonic crystals filled with polymers, Applied Physics Letters 2006, 88: 161112-1-161112-3.
Buswell, SC, et al., Specific detection of proteins using photonic crystal waveguides, Optics Express 2008, 16: 15949-15957.
Lee, S., et al., Improved Localized Surface Plasmon Resonance Immunoassay with Gold Bipyramid Substrates, Anal. Chem. 2009, 81: 4450-4455.
Letant, SE, et al., Most-Probable-Number Rapid Viability PCR method to detect viable spores of *Bacillus anthracis* in swab samples, Journal of Microbiological Methods 2010, 81: 200-202.
Kane, SR, et al., Rapid, high-throughput, culture-based PCR methods to analyze samples for viable spores of *Bacillus anthracis* and its surrogates, Journal of Microbiological Methods 2009, 278-284.
Lin, S., et al., Design of nanoslotted photonic crystal waveguide cavities for single nanoparticle trapping and detection, Optics Letters 2009, 34: 3451-3453.
Alexander, T., et al., Characterization of a commercialized SERS-active substrate and its application to the identification of intact *Bacillus* endospores, Applied Optics 2007, 46: 3878-3890.
Asano, T., et al., Analysis of the experimental $Q$ factors (~1 million) of photonic crystal nanocavities, Optics Express 2006, 14: 1996-2002.

* cited by examiner

Diamond structure, Si

Schrödinger's equation $$\hat{H}|\psi\rangle = E \cdot |\psi\rangle$$

$$\hat{H} = -\frac{\hbar^2}{2m}\nabla^2 + V(\vec{r})$$

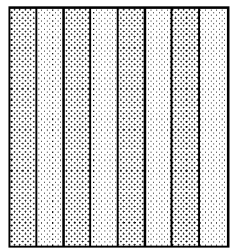
**FIG. 2A
(PRIOR ART)**
Maxwell equations
$$\nabla \times \left[\frac{1}{\varepsilon(r)} \nabla \times H(r)\right] = \left[\frac{\omega}{c}\right]^2 H(r), \text{ where } \varepsilon(r) = \varepsilon(r+R)$$
**FIG. 2B
(PRIOR ART)**
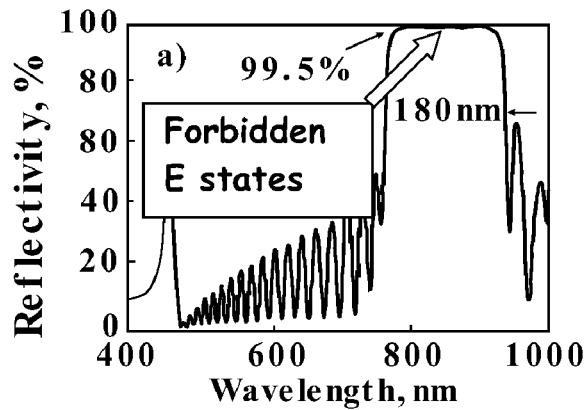
**FIG. 2C
(PRIOR ART)**

MULTIPLEXED PHOTONIC MEMBRANES AND RELATED DETECTION METHODS FOR CHEMICAL AND/OR BIOLOGICAL SENSING APPLICATIONS

CROSS REFERENCE TO RELATED APPLICATIONS

The present application claims the priority benefit of U.S. Provisional Application 60/993,740 filed on Sep. 13, 2007, which is incorporated herein by reference in its entirety.

FIELD

The present disclosure relates to photonic membranes. More in particular, it relates to flow through photonic membranes for chemical and/or biological sensing applications and related detection methods.

BACKGROUND

Recently, interest has emerged in label-free optical affinity-based biosensors, which allow to study bio-organisms without fluorescence or radiolabels, and thus dramatically simplify assays. Typically, affinity-based biosensors detect the presence of a target molecule by selective binding to a capture probe. For optical biosensors, binding translates into a change of optical properties, i.e. the complex refractive index or luminescence.

Optical detection methods based on complex refractive index transduction include interferometry in micro and nano-fabricated devices, including porous thin films, Bragg reflectors, and microcavities, all of which require an optical measurement system with large beams and sensing areas (about 1 mm$^2$). See E. Chow, A. Grot, L. W. Mirkarimi, M. Sigalas, and G. Girolami, Ultracompact biochemical sensor built with two-dimensional photonic crystal microcavity, Optics Letters 29, 1093 (2004); L. L. Chan, B. T. Cunningham, P. Y. Li, D. Puff, Self-referenced assay method for photonic crystal biosensors: Application to small molecule analytes, Sens. Actuators B 120, 392 (2007); V. S.-Y. Lin, K. Motesharei, K. Motesharei, K.-P. S. Dancil, M. J. Sailor, and M. R. Ghadiri, Science 278, 840 (1997); F. Morhard, J. Pipper, R. Dahint, and M. Grunze, Sens. Actuators B 70, 232 (2000); M. Loncar, A. Scherer, and Y. Qiu, Appl. Phys. Lett. 82, 4648 (2003).

Within this scenario, photonic crystals constitute an emerging alternative technology, due to their powerful light-confinement abilities which would enable local, and therefore, sensitive, refractive index measurements.

Extensive work has been performed during the last fifteen years to build and investigate photonic crystals, the optical analogues to electronic semiconductors. In semiconductors electrons propagate in a periodic potential, which originates from the atomic lattice. This modifies the dispersion of free electrons and opens a bandgap in the energy diagram, as shown in FIGS. 1A-1C.

In particular, FIGS. 1A-1C show electron dispersion in semiconductors. FIG. 1A shows a periodic lattice for Si. FIG. 1B shows the induced periodic potential affecting the allowed electron energy states, and Schrödinger's equation describing the quantum mechanical properties of electrons in a crystalline solid. FIG. 1C shows how solutions of the equations result in a bandgap diagram with two allowed energy bands (valence band and conduction band) separated by a forbidden band also called electronic band gap.

Photonic crystals are materials built to present a periodic variation of refractive index. The periodicity being of the same order of magnitude as the wavelength of the electromagnetic (EM) waves, these structures exhibit band gaps for photons, as indicated in FIGS. 2A-2C, where photon dispersion in a 1D photonic crystal is shown. In particular, FIG. 2A shows the 1D periodic permittivity distribution, FIG. 2B shows the Maxwell's equation describing the electromagnetic properties of photons in a medium of periodic refractive index, and FIG. 2C shows how solutions of the equation result in the opening of a forbidden band for the energy states of the photons, also called photonic bandgap.

Most of these devices are designed with opto-electronic applications in mind and despite a recent step in the bio-sensing direction with blind 1D structures (see Schmidt, B., Alemeida, V., Manolataou, C., Prebel S., & Lipson, M., Nanocavity in a silicon waveguide for ultrasensitive detection, Appl. Phys. Lett. 85, 4854 (2004)), and non-specific chemical detection with blind 2D crystals, no selective chemical or biological detection has ever been reported with a 2D photonic platform (see the previously mentioned paper and also Levine, M. J. et al. Zero-mode waveguides for single molecule analysis at high concentration, Science, 299 (2003)).

The ability to manipulate photonic bandgaps in the crystals by design offers the possibility of engineering highly resonant structures, and therefore high-Q microcavities, which makes photonic crystals attractive candidates for ultra compact, highly sensitive assays. Over a few µm$^2$ sensing area a few fL amount of sample analyte could be studied, providing the backbone for a very dense platform with single organism detection limit (lab-on-chip).

The various schemes and diagrams of FIG. 3 show a 1D photonic bio-sensing platform designed by Fauchet et al. (see M. R. Lee, and P. M. Fauchet, Nanoscale microcavity sensor for single particle detection, Optics Lett. 32, 3284 (2007)—S. Chan, S. R. Horner, P. M. Fauchet, & B. L. Miller, Identification of Gram negative bacteria using nanoscale silicon microcavities, J. Am. Chem. Soc. 123, 11797 (2001)).

The top scheme of FIG. 3 describes the device layout in which a 1D photonic structure is electrochemically etched on a silicon wafer. Layers of porous silicon with alternating high and low porosities constitute distributed Bragg reflectors (DBRs) around a luminescent central layer, also called cavity. The entire assembly rests on the silicon substrate. The data shown in the four center diagrams of FIG. 3 corresponds to the luminescence of a series of cavities filtered by the surrounding DBRs and collected on the top of the device.

The darker lines of the two upper center diagrams are data collected after functionalization of the device with TWCP (tetratryptophan ter-cyclo pentane), a molecule that selectively binds lipid A present in the viral coat of Gram(−) bacteria. The lighter lines of the two upper center diagrams are data collected after exposure of the functionalized device to Gram(−) bacteria (right) and Gram(+) bacteria (left). The lines of the two lower diagrams represent the difference between the darker and lighter lines discussed above and allow to measure the spectral shift in photonic band gap resulting from the increase of refractive index in the DBRs upon binding of bacteria. The data is summarized in the bottom table of FIG. 3, indicating that no shift occurred upon exposure to Gram(+) bacteria while a 3-4 nm shift occurred upon exposure to 2 µg of Gram(−) bacteria.

Although it provides a proof of concept for the use of chemically functionalized 1D photonic crystals for bio-organism detection, the device presented on FIG. 3 requires the binding of a minimum of 2 µg of bacteria (thousands of organisms) to generate a positive signal. Indeed, the detection limit for a porous silicon crystal is inherently high because transduction is generated by a change of effective refractive index that has to occur across the entire volume of the crystal.

Functionalized silicon membranes were fabricated by electrochemistry and their ability demonstrated to selectively capture simulated bio-organisms. A photonic membrane can be defined as a photonic crystal formed of a periodic array of through-holes fabricated in a free-standing membrane waveguide, where the refractive index of the membrane material is larger than the refractive index of the surrounding air or liquid. A photonic membrane provides strong confinement of light both along and perpendicularly to the plane of the membrane. In particular, FIG. 4 shows SEM pictures (top view in the background and cross section in the center) of a silicon membrane with 2 μm pores prepared by electrochemistry. This device was chemically functionalized with antibodies and selective capture of antigen-functionalized beads (see central sphere in the bottom inset) was demonstrated. See Letant, S. E., Hart, B. R., van Buuren, A. W. & Terminello, L. J. Functionalized silicon membranes for selective bio-organism capture, Nature Materials 2, 391 (2003).

Through channels or pores with diameters ranging from a few hundreds of nanometers to many microns were etched on pre-patterned silicon substrates and covalently functionalized with antibodies (see Letant, S. E., Hart, B. R., Kane, S. R., Hadi, M., Shields, S. M. & Reynolds, J. G. Enzyme immobilization on porous silicon surfaces, Adv. Mat. 16, 689 (2004) and Hart, B. R., Letant S. E. et al. New method for attachment of biomolecules to porous silicon, Chem. Comm. 3, 322 (2003)), in order to add chemical specificity to size selectivity. See also U.S. Pat. No. 7,155,076, incorporated herein by reference in its entirety.

The ability of the functionalized membranes to capture simulated bio-organisms was then successfully tested (as shown in FIG. 4 and in the related paper and patent mentioned above).

SUMMARY

According to a first aspect, a photonic detection system is provided, comprising: a photonic membrane with through pores, the through pores having inner walls to which chemical or biological target specific anchors are adapted to be attached; an optical input to the photonic membrane; and an optical output detecting arrangement connected with the photonic membrane, wherein the through pores are distributed on the photonic membrane along multiple regions of through pores, through pores pertaining to a first region having inner walls to which a first type of chemical or biological target specific anchor is attached, through pores pertaining to a second region having inner walls to which a second type of chemical or biological target specific anchor is attached, and so on.

According to a second aspect, a photonic detection system is provided, comprising: a plurality of photonic membranes stacked on each other, each photonic membrane having through pores, the through pores having inner walls to which chemical or biological target specific anchors are adapted to be attached; an optical input arrangement to the plurality of photonic membranes; and an optical output detecting arrangement connected with the photonic membranes, wherein the through pores are distributed on each of the photonic membranes along multiple regions of through pores, through pores pertaining to a first region having inner walls to which a first type of chemical or biological target specific anchor is attached, through pores pertaining to a second region having inner walls to which a second type of chemical or biological target specific anchor is attached and so on, and a diameter of the through pores of the first photonic membrane is larger than a diameter of the through pores of the second photonic membrane, the diameter of the through pores of the second photonic membrane is larger than a diameter of the through pores of a third photonic membrane and so on.

According to a third aspect, a method of detecting target organisms of an analyte comprising non-target organisms and said target organisms is provided, the method comprising: flowing the analyte through a photonic membrane with through pores, the through pores having inner walls to which chemical or biological target specific anchors are adapted to be attached, the through pores being distributed on the photonic membrane along multiple regions, through pores pertaining to a first region having inner walls to which a first type of chemical or biological target specific anchor is attached, through pores pertaining to a second region having inner walls to which a second type of chemical or biological target specific anchor is attached, and so on; and photonically detecting said target organisms through binding of said target organisms with one or more of said chemical or biological target specific anchor.

According to a fourth aspect, a method of detecting target organisms of an analyte comprising non-target organisms and said target organisms is provided, the method comprising: flowing the analyte through a plurality of photonic membranes stacked on each other, each photonic membrane having through pores, the through pores having inner walls to which chemical or biological target specific anchors are adapted to be attached, the through pores being distributed on of each the photonic membranes along multiple regions of through pores, through pores pertaining to a first region having inner walls to which a first type of chemical or biological target specific anchor is attached, through pores pertaining to a second region having inner walls to which a second type of chemical or biological target specific anchor is attached and so on, wherein a diameter of the through pores of the first photonic membrane is larger than a diameter of the through pores of the second photonic membrane, the diameter of the through pores of the second photonic membrane is larger than a diameter of the through pores of a third photonic membrane and so on; and photonically detecting type of said target organisms through binding of said target organisms with one or more of said chemical or biological target specific anchors, and size of said target organisms through the diameter of the one or more pores associated with said one or more anchors.

According to a fifth aspect, a flow through photonic membrane is provided, comprising: through pores, the through pores having inner walls to which chemical or biological target specific anchors are adapted to be attached, the through pores distributed on the photonic membrane along multiple regions of through pores, through pores pertaining to a first region having inner walls to which a first type of chemical or biological target specific anchor is attached, through pores pertaining to a second region having inner walls to which a second type of chemical or biological target specific anchor is attached, and so on.

Further embodiments of the present disclosure can be found in the written specification, drawings and claims of the present application.

According to an embodiment of the present application, Applicants show a 2D photonic crystal, in particular a 2D flow through photonic membrane, in which the refractive index periodicity is constituted of alternating layers of bulk silicon and air (well defined channels). This design leads to a dramatic reduction of the detection limit since the device is sensitive to local changes of refractive index in each channel (by opposition to the effective refractive index change that has to occur across the entire porous silicon structure shown on FIG. 3), ultimately leading to single organism detection capabilities for these platforms.

The teachings of the present disclosure provide a viable solution to technology gaps in the Biological Warfare (BW) and Chemical Warfare (CW) detection areas. A real-time capability has been identified to detect, identify, characterize, locate, and warn against BW (and CW) agent threats. The proposed devices and methods combine collection, concentration, and detection of differently sized bio-organisms or chemical agents onto a single platform: an integrated system of photonic waveguiding silicon membranes.

The approach of the present disclosure eliminates the current spatial and temporal disconnection between on-field sample collection and laboratory analysis. Because of the strong light-confinement properties of photonic crystal microcavities (high quality factor, or high-Q), it is expected that detection is allowed down to a single organism and will only require a very small sensing area (~10-100 $\mu m^2$) and very small amounts of sample (~1-10 fL). In addition, since the membrane allows flow-through, Applicants also expect that much larger volumes of analyte can be accommodated when available, and even further promoted by a three-dimensional staggered filtration architecture. A further advantage of the flow-through geometry according to the present disclosure is that it improves the binding probability of the target organism to the molecular probes anchored on the pore walls.

BRIEF DESCRIPTION OF THE DRAWINGS

FIGS. 2A-2C show photon dispersion in a 1D photonic crystal.

DETAILED DESCRIPTION

Figure 1A:
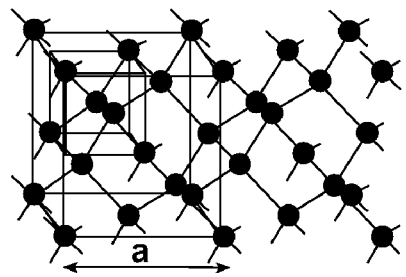
FIGS. 1A-1C show electron dispersion in semiconductors.
Figure 1B:
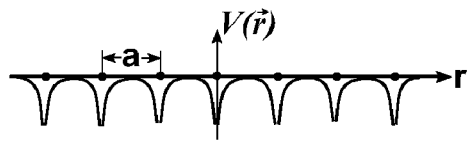
Figure 1C:
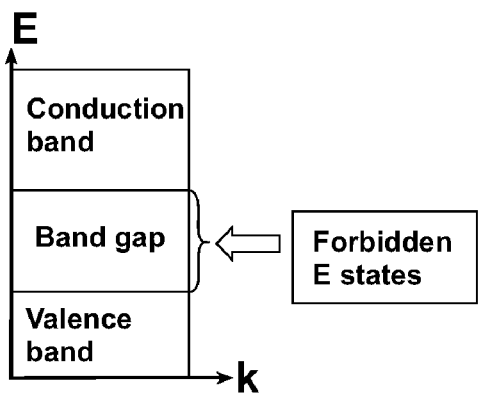
Figure 3:
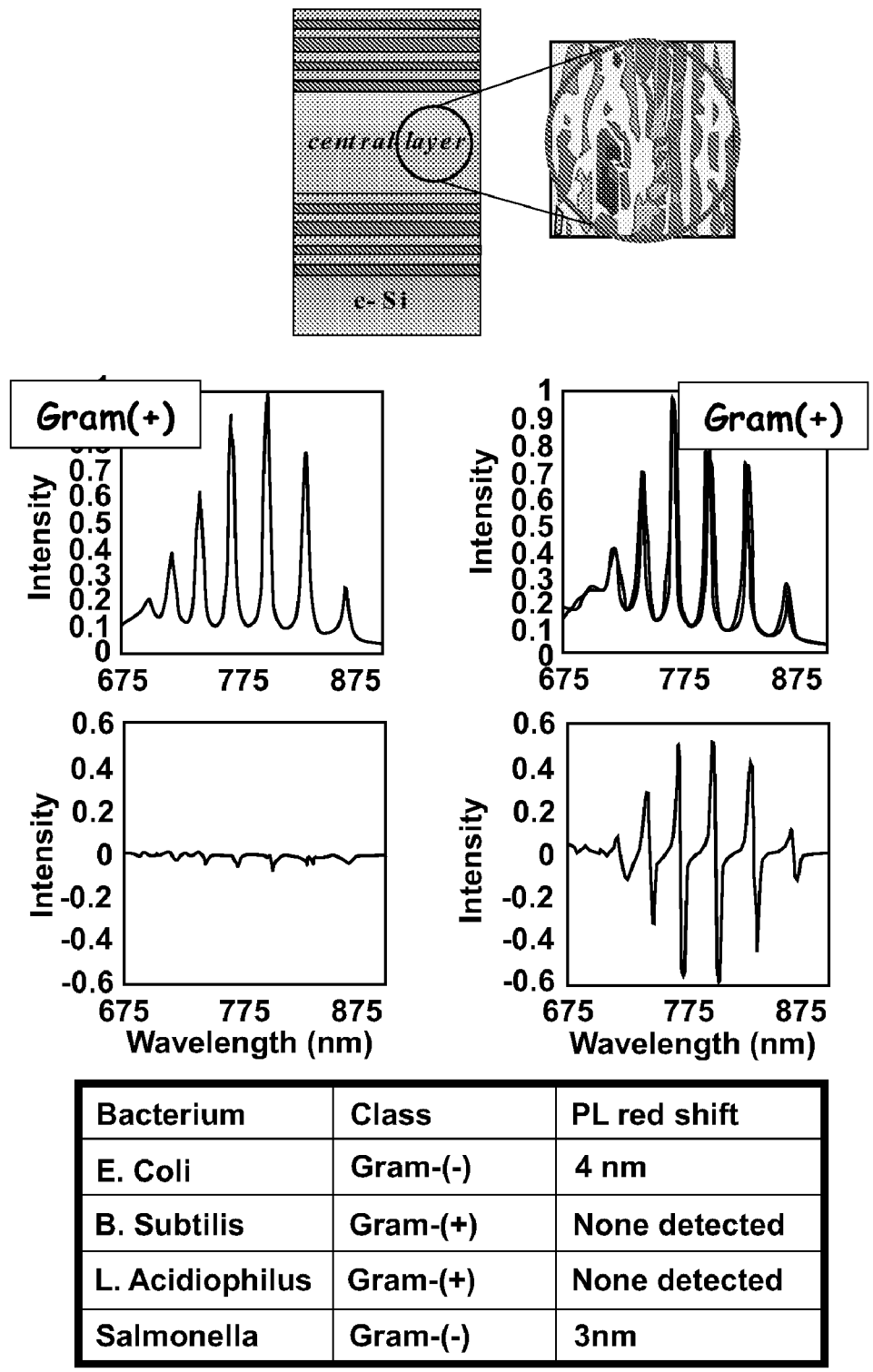
FIG. 3 shows a chemically functionalized 1D photonic crystal for bio-organism detection.
Figure 4:
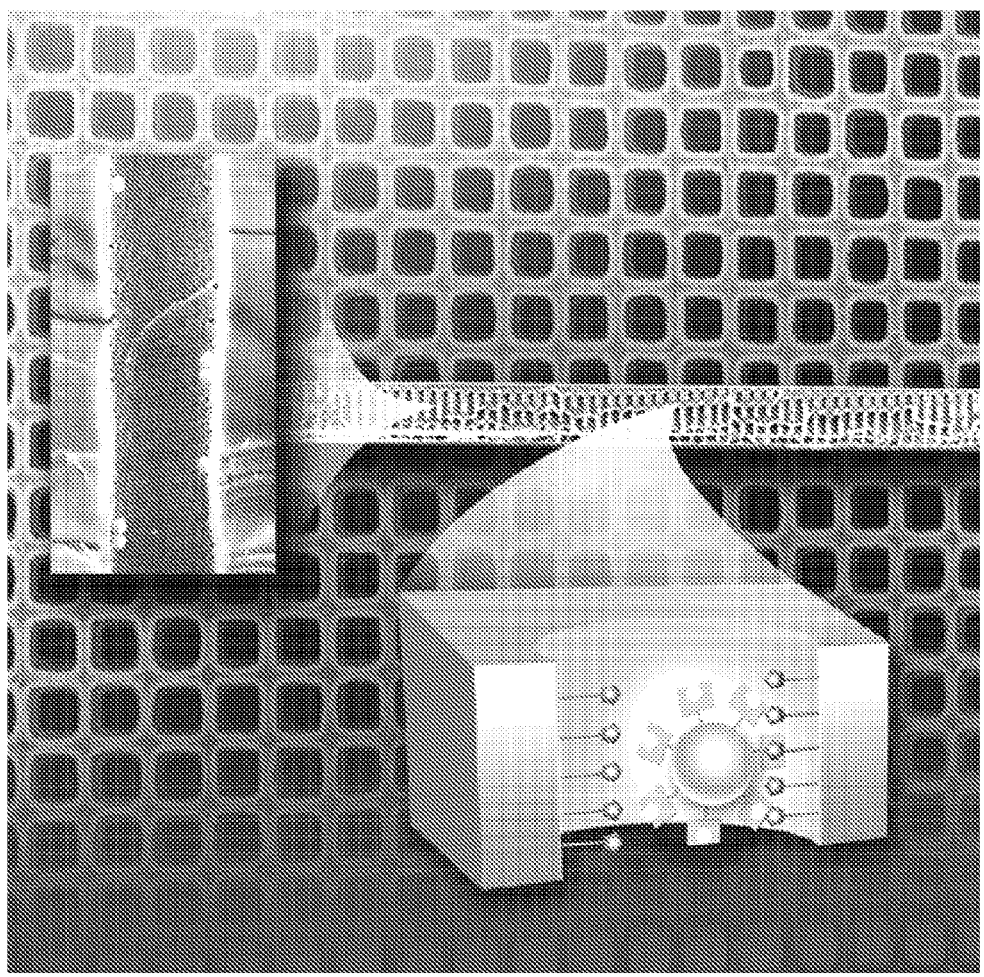
FIG. 4 shows schematic representations of a functionalized membrane and its ability to capture organisms.
Figure 5:
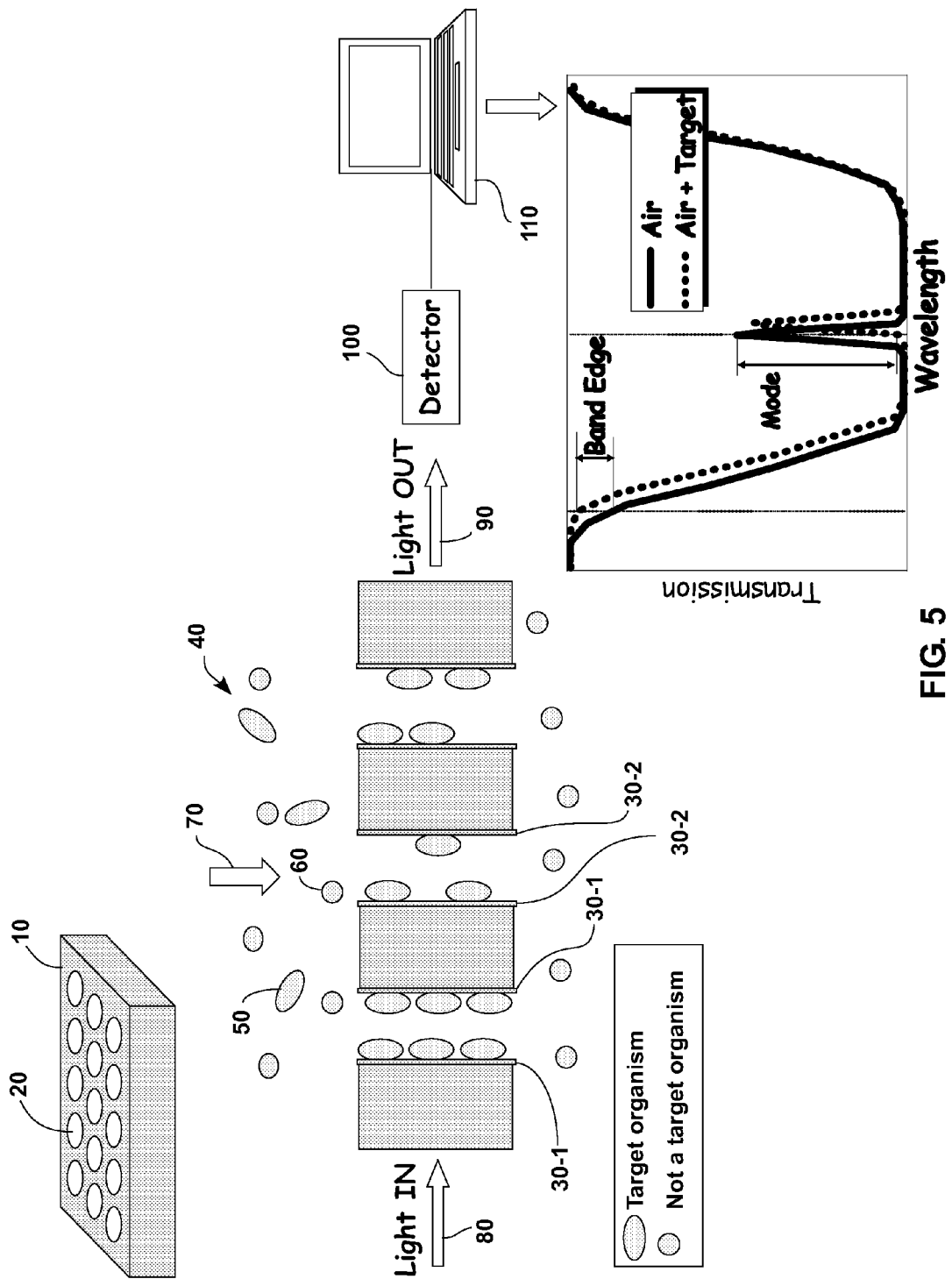
FIG. 5 shows a single-membrane embodiment of the present disclosure.

FIG. 5 shows a schematic representation of one of the embodiments of the present disclosure, where a stand-alone photonic membrane comprising a flow-through silicon crystal (10) is shown both in top perspective view (top portion of the figure) and cross sectional view (middle portion of the figure). The membrane (10) comprises a plurality of channels or pores (20). Each channel or pore (20) has channel walls (30). The channel walls (30) are chemically functionalized with specific probes which allow binding of some chemical and/or biological agents. According to one embodiment of the present disclosure, as better shown in the middle portion of FIG. 5, channel walls (30-1) of a first row of channels can be functionalized with a first probe to be receptive of a first kind of target organism, channels walls (30-2) of a second row of channels can be functionalized with a second probe to be receptive of a second kind of target organism, and so on. Therefore, each time an analyte (40) comprising target organisms (50) and no-target organisms (60) flows (70) through the membrane (10), the target organisms (50) can be detected in view of binding of these organisms on one or more of the channel walls.

In particular, during the analyte flow (70), light is input (80) into the photonic membrane (10) and output (90) from the photonic membrane (10). The output light (90) is detected through a detector (100) and the results evaluated through a data processing system (110). In particular, as shown in the bottom graph of FIG. 5, at a given wavelength, the photonic band gap experienced by light when encountering a point defect translates into different values of light intensity, depending on whether a target is not bound or is bound to the channel walls. Coupling of light into a photonic membrane and further detection is known as "end-fire coupling technique." Membrane pores functionalization and the end-fire coupling technique are known per se from the already mentioned U.S. Pat. No. 7,155,076, which is incorporated herein by reference in its entirety.

As shown in the embodiment of FIG. 5, several different chemical agents or bio-organisms can be collected in a combined way on a single device. This allows analysis to be performed in the field in real time. Moreover, the preparation of the sample to be detected through the membrane of FIG. 5 is minimal, due to PCR-free, label-free whole organism detection technique. 3) enhanced collection due the flow-through design, 4) selectivity provided by surface functionalization with Molecular Recognition Elements such as natural or synthetic antibodies, 5) dramatic sensitivity improvement due to the use of a 2D photonic crystal and to the possibility of engineering high-Q optical microcavities by introducing point and line or region defects, 6) easy implementation of multiplexed bio-organism detection on a chip, 7) compatibility of interrogation wavelengths with high speed telecommunication systems readily available.

Figure 6:
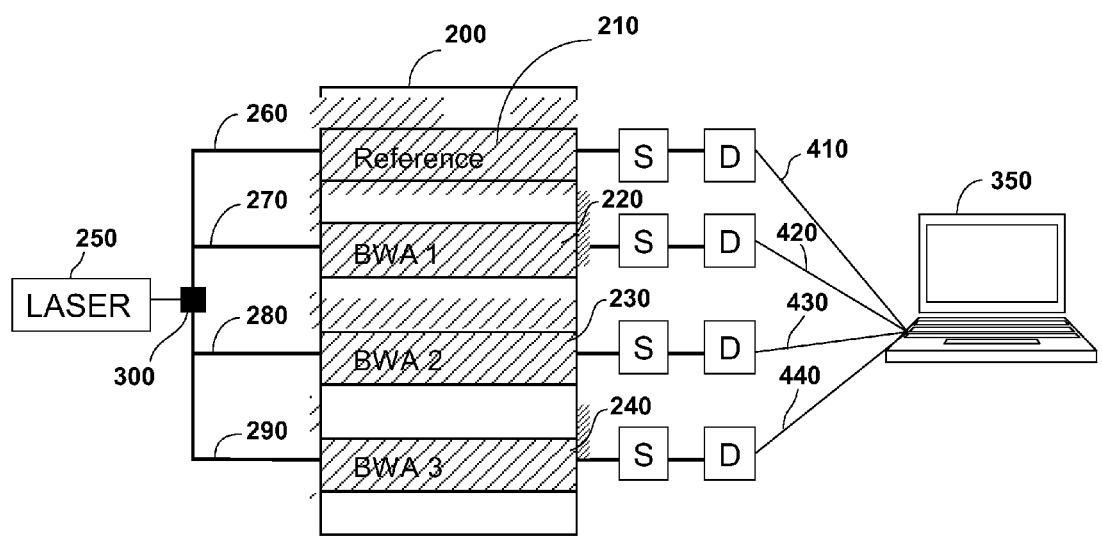
FIG. 6 shows a single-membrane embodiment with light input, detection and processing architecture.

FIG. 6 shows a further embodiment of the present disclosure. As shown in the top view of the figure, a photonic membrane (200) comprises a plurality of regions (210, 220, 230, 240), each region including a plurality of through holes (as later shown in FIG. 7), grouped into a plurality of regions, e.g., lines.

Figure 7:
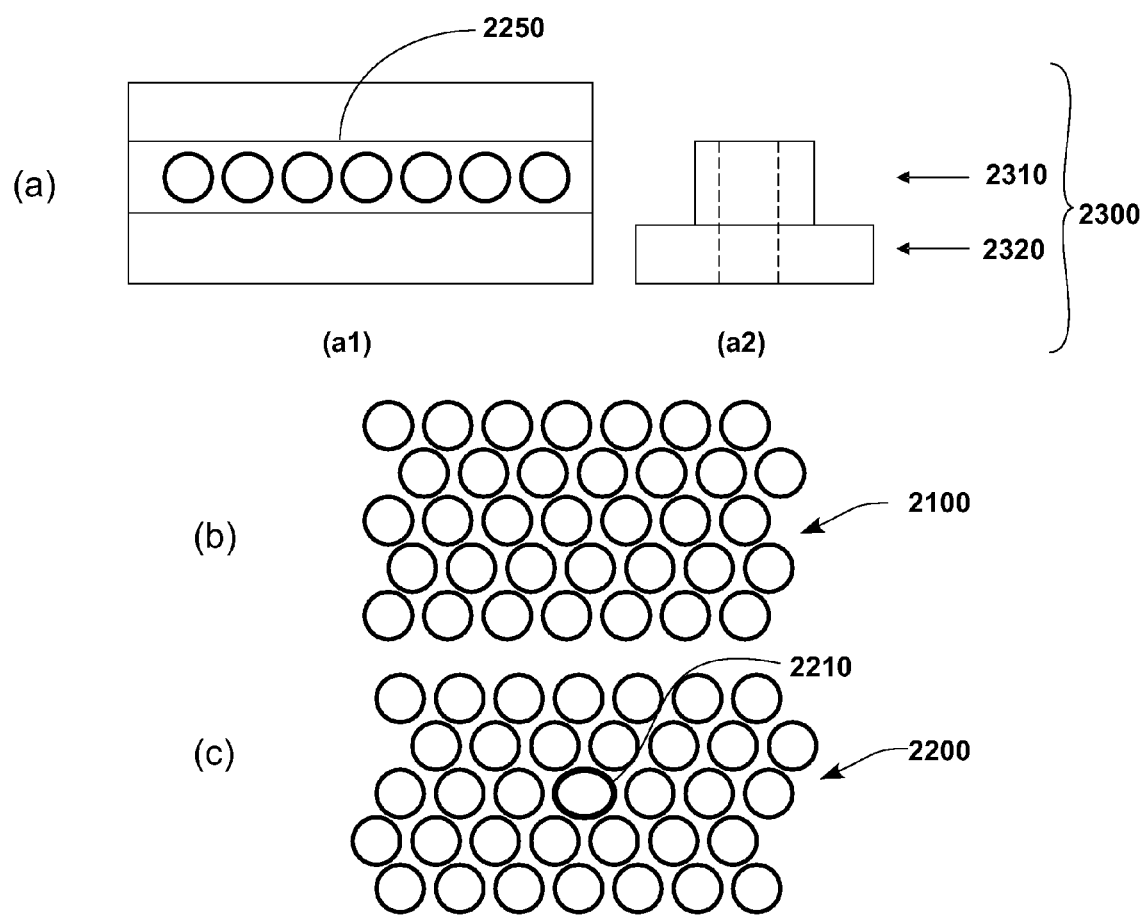
FIG. 7 shows some possible through hole arrangements for the embodiment of FIG. 6.

FIG. 7 shows three possible arrangements for each region (210, 220, 230, 240). In the arrangement (a) of FIG. 7 the through holes are distributed around a single region, e.g., a line. In particular, section (a1) shows a top view of the membrane and section (a2) shows a bottom view of the membrane. Each line of pores (2250) has a ridge geometry (2300), comprised of a waveguide section (2310) and a cladding section (2320). In the arrangement (b) of FIG. 7, a region can comprise a perfect photonic crystal (2100) including an array of through pores. In the arrangement (c) of FIG. 7, a region can include a photonic crystal (2200) comprising an array of pores and a defect (2210). The defect (2210) can be, for example, a pore with a different diameter, or a removed pore.

Similarly to what explained in FIG. 5, each region (210, 220, 230, 240) of FIG. 6 can be functionalized in a different manner. The first line or row (210) can be a reference row, where the channel walls are not functionalized. The second row (220) can have channel walls functionalized for bonding with a first Bio-Warfare Agent BWA1 (it could also be a chemical agent). The third row (230) can have channel walls functionalized for bonding with a second agent BWA2, and so on. A light source (250), e.g. a continuous wave laser diode source, is split into a plurality of optic fibers (260, 270, 280, 290) by way of a splitter (300). One or more output fibers can send the signal to a compact multi-channel spectrometer, represented in FIG. 6 as a plurality of units (S). A plurality of detecting units (D), each corresponding to a respective row, can be located downstream of the membrane (200). A processor (350), e.g. a laptop computer, can compare the signal of each functionalized line (420, 430, 440) to the un-functionalized reference line (410) by way of differential measurement in order to suppress noise and interferences, and then analyze the data to allow bio-organism identification. In case a compact embodiment is desired, the spectrometer can be powered by the laptop batteries. In such embodiment, the size and weight of the overall system could be a few cubic feet and below 2 pounds. Future designs can provide an arrangement in which the system is fully integrated on a single platform compatible with CMOS readout circuitry designed for lab-on-a-chip applications.

With reference to the embodiments of FIGS. 6 and 7, the person skilled in the art will understand that each region (210, 220, 230, 240) of FIG. 6 can have any one of the arrangements (a), (b), (c) shown in FIG. 7. Also, each region can have through pores having a different diameter or shape than the through pores of other regions.

The transmission of light through the photonic crystal can be recorded before and after binding of the organisms using the end-fire technique described with reference to FIG. 5. In particular, upon binding of the beads in the channels of the flow-through photonic crystal, the refractive index of the channels will increase and the transmission curve will shift, the amplitude of the shift depending on the channel volume occupied by simulated bio-organisms. Comparison of the transmission curves recorded before and after binding of various concentrations of antigen-coated beads (for both virus and bacteria size regimes) can be used to determine the experimental detection limit in both dry and aqueous phase.

The membrane in accordance with the embodiments of FIG. 5 and FIG. 6 can be operated according to two different approaches. In a first mode of operation, a white light source is used in combination with a spectrometer to evaluate the wide bandgap of the membrane (of the order of 100s of nm). In this way, a full spectral trace of the photonic bandgap is provided. Such spectral trace can be used for general device characterization and for sensing in perfectly periodic photonic crystals, in which the binding of the target in a pore is transduced by a spectral shift of the broad band edge feature. In a second mode of operation, a monochromatic light, e.g. a compact laser, is used in combination with the detectors (e.g., high sensitivity detectors possibly integrated with narrow band filters) placed at the output, to measure narrow resonances (expected to be a few nm) and relative changes induced by inserted defects. Usually, this second mode of operation is more sensitive and needs less power.

Figure 8:
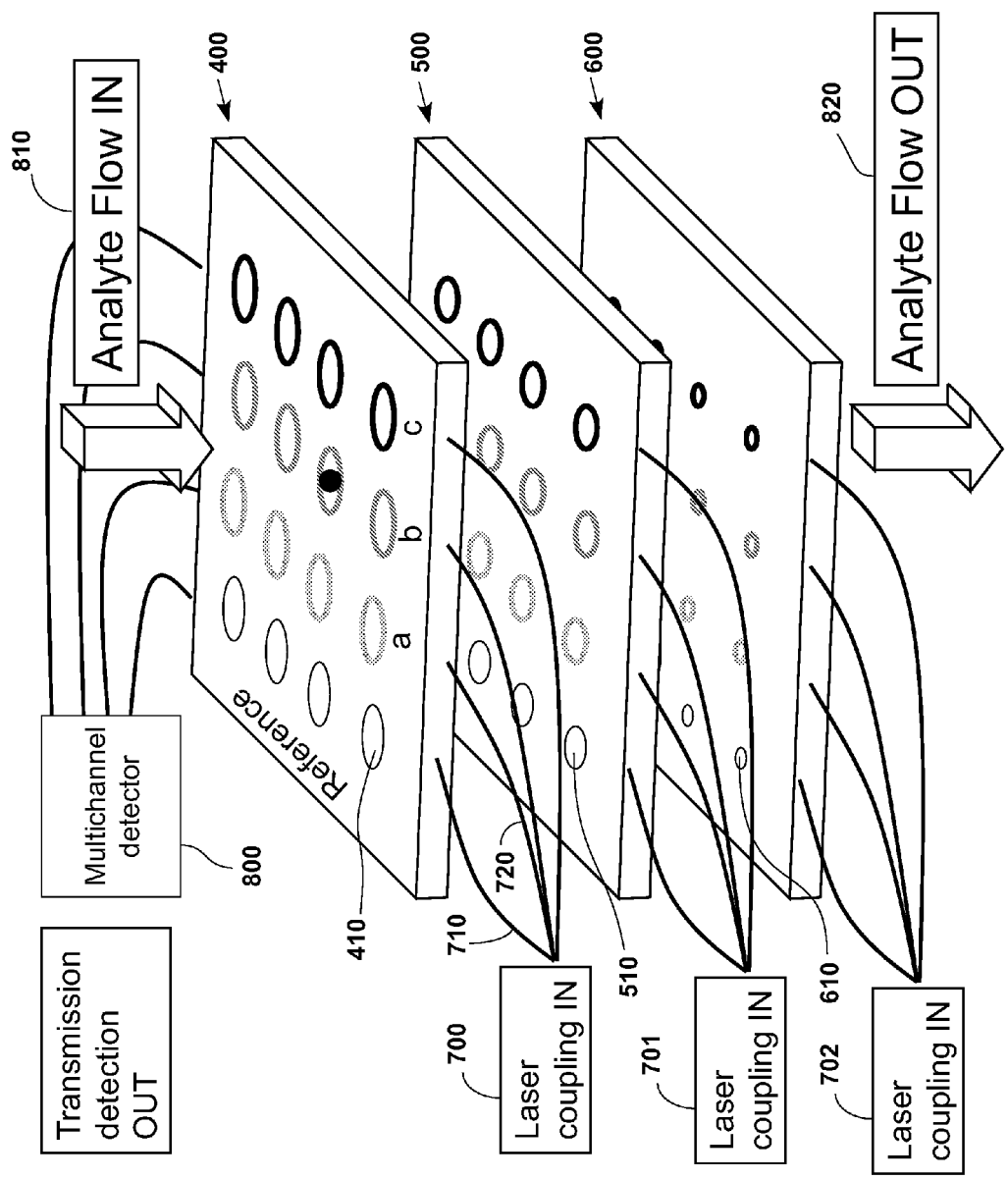
FIG. 8 shows a multiple-membrane embodiment of the present disclosure.

A further embodiment of the present disclosure is shown in FIG. 8, where vertically stacked photonic membranes with various channel sizes are shown. Throughout the following description of FIG. 8, reference will be made to through pores having an arrangement similar to the arrangement (a) of FIG. 7. However, the person skilled in the art will understand that also through pores according to the arrangements (b) and (c) of FIG. 7 can be provided. Turning to the embodiment of FIG. 8, such figure shows, by way of example, three vertically stacked membranes (400, 500 and 600). Each membrane comprises a row of reference pores (410, 510, 610) and a plurality of functionalized rows (420, 520, 620; 430, 530, 630; 440, 540; 640). The diameter of the pores of membrane (500) is smaller than the diameter of the pores of membrane (400). Similarly, the diameter of the pores of membrane (600) is smaller than the diameter of the pores of membrane (500).

According to an embodiment of the present disclosure, a first line (410) of through pores of a first photonic membrane (400) is in spatial correspondence with a first line (510) of through pores of a second photonic membrane (500). Similarly, a second line (420) of through pores of the first photonic membrane (400) is in spatial correspondence with a second line (520) of through pores of the second photonic membrane (500) and so on.

As shown in FIG. 8, and similarly to what previously shown in FIG. 6, each membrane is connected to an input light source (700, 701, 702, respectively) by way of input fibers (710, 720, 730, 740). On the output side, a multichannel detector (800) is provided. The flow of the analytes is from the top (810) to the bottom (820). According to an embodiment of the present disclosure, one detector per membrane is provided, in view of the fact that the wavelength is different for each membrane of the stack of membranes. In particular, the wavelength should match the photonic bandgap, which itself depends on the size of the pores and the period of their arrangement. The detector can be a multichannel detector so that it can receive multiple inputs (coming from the multiple lines) for each membrane.

In this way, a progression of pore diameters, starting, for example, from large bacteria-sized channels and progressively reduced, for example, to virus size, is obtained. Such geometry also reduces the clogging probability while allowing multiplexing. Moreover, the size of the organism can be determined vertically and chemical composition of the coat can be detected horizontally (for each size range, various antibodies can be anchored on parallel channel rows). The structure of FIG. 8 can be used, for example, for full bio-organism identification, or for signature generation on unknown threat organisms.

With reference to the embodiments of the previous figures, the applicants believe that no more than 10 pores are necessary in each row to open the photonic band gap. According to an embodiment of the present disclosure, a possible number of pores would be 5-10 per line. The number of pores per line is subject to competing conditions: on one side more pores provide a long range periodicity and, therefore, a well defined photonic band gap; on the other side, more pores also imply a longer distance for the photons to travel and, therefore, a higher probability of losses. Point defects can also be inserted in each row to engineer and control modes in the photonic band gap.

If a bio-organism (represented by the bead (850) in FIG. 8) binds in the structure, the location of the binding will provide information on the organism size and bio-organism family. For example, the bio-organism (850) is bound on membrane (400), which would mean, for example, that is a bacterium with a 200 nm diameter, and is bound on row (430), which would mean that it binds on the antibody provided on the surface walls of pores (430).

The wavelength of the light used in the embodiments of the previous figures can also be an ultraviolet (UV) or near-infrared (IR) frequency.

Each photonic waveguide slab or membrane can be made, for example, of silicon or other materials such as SiONy, SiOx, SiC, GaN, PbTe and, more generally, oxides, III-V or II-VI semiconductors, and polymers. Various interrogation wavelengths can be used across the device, as already explained above. In particular, smaller pore sizes mean a photonic bandgap at a lower wavelength. As also mentioned before, a broad source can be used to record the entire band gap transmission, while a single wavelength can be used to interrogate specific modes in the photonic band gap. The device can be used for biological (bacteria, viruses, toxin) and chemical sensing.

Future applications can also include the generation of fingerprints for the detection and classification of non-traditional agents and emerging threat agents. In particular, the system according to the present disclosure could be trained like artificial noses. In other words, a very broad set of known organisms would be tested and the corresponding data stored in a database. When an unknown sample is processed by the membrane stack, the data can be analyzed via PCA (Principal Component Analysis) and compared to the database. The data from the entire device stack (all the lines, from all the stacks) can be seen as a fingerprint.

Figure 9:
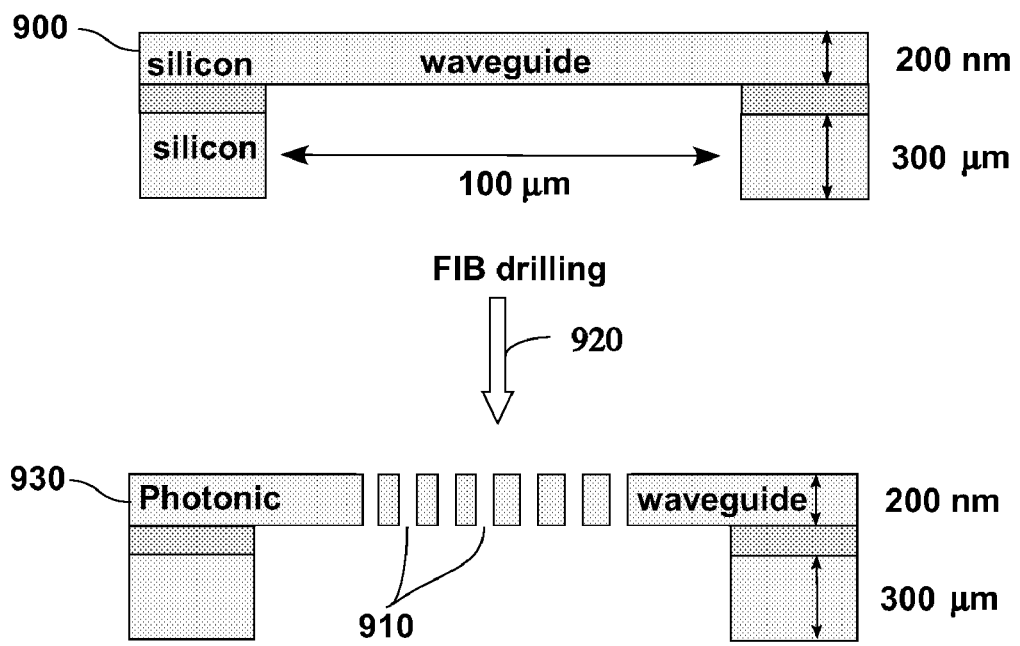
FIG. 9 shows an exemplary method of fabrication of the flow through membrane of the present disclosure.

FIG. 9 shows an exemplary method of fabrication of the membrane of the present disclosure. In particular, silicon on insulator (SOI) wafers (having, for example, a device layer thickness of 200 nm) can i) be optionally coated with silicon nitride, ii) patterned by standard photolithography techniques, and iii) etched (e.g., by deep reactive ion etching, DRIE) in order to obtain free-standing 200 nm thick silicon waveguides (900) which will allow, for example, a single mode propagation at 1.55 μm. A periodic pattern of through channels (910) can then be drilled on the waveguide by focused ion beam (FIB) (920), to open a photonic band gap into the waveguide and convert the silicon waveguide (900) into a flow-through photonic silicon membrane (930). With the FIB technique there is no limitation on the geometry of the drilled pattern or on the dimensions of the channels (910), above a 1:10 (channel diameter:membrane thickness) aspect ratio. Moreover, for the small patterns contemplated by the present disclosure, FIB constitutes a fast (under an hour for an array of 10×10 channels) and versatile technique as no mask has to be designed. A change in the pattern to test theoretical predictions can be achieved in a matter of minutes at no cost by reprogramming the drilling sequence while it would take days and money to design new masks when using lithography techniques. Moreover, FIB drilling gives access to channel diameters ranging from nanometers to many microns, while standard lithography is limited to a few hundreds of nanometers.

Accordingly, what has been shown are photonic membranes for detection of biological and/or chemical organisms and related detection methods. While the membranes and methods have been described by means of specific embodiments and applications thereof, it is understood that numerous modifications and variations could be made thereto by those skilled in the art without departing from the spirit and scope of the disclosure. It is therefore to be understood that within the scope of the claims, the disclosure may be practiced otherwise than as specifically described herein.

What is claimed is:
1. A photonic detection system comprising:
a photonic membrane with through pores, the through pores having inner walls to which chemical or biological target specific anchors are adapted to be attached;
an optical input to the photonic membrane; and
an optical output detecting arrangement connected with the photonic membrane,
wherein the through pores are distributed on the photonic membrane along multiple regions of through pores, through pores pertaining to a first region having inner walls to which a first type of chemical or biological target specific anchor is attached, through pores pertaining to a second region having inner walls to which a second type of chemical or biological target specific anchor is attached, and so on,
wherein the photonic membrane comprises an additional region of through pores to which no chemical or biological target specific anchors are attached, and
wherein measurement of a detection output of the photonic detection system occurs differentially, by subtraction of a detection output of the additional region of through pores from a detection output of each region of through pores.

2. The system of claim 1, wherein the optical input to the photonic membrane comprises a plurality of optical input lines, one for each region of through pores.

3. The system of claim 1, wherein the optical output detecting arrangement comprises a plurality of detectors, one for each region of through pores.

4. The system of claim 1, wherein the optical input is a laser light.

5. The system of claim 1, wherein the optical detecting arrangement is a multichannel detector.

6. The system of claim 1, wherein the optical detecting arrangement is connected with a processing unit downstream of the photonic membrane.

7. The system of claim 6, wherein the processing unit is a portable computer.

8. The system of claim 1, wherein the photonic membrane is a silicon photonic membrane.

9. The system of claim 1, wherein the multiple regions of through pores are shaped differently from each other.

10. The system of claim 1, wherein each region of through pores is selected from the group consisting of: a line of through pores with a ridge geometry, a perfect photonic crystal comprising an array of through pores, and a photonic crystal comprising an array of through pores and a defect.

11. The system of claim 10, wherein the defect is selected from the group consisting of: a pore with a different diameter or shape than the remaining through pores of the array, and a removed pore.

* * * * *